US007282580B2

United States Patent
Singh et al.

(10) Patent No.: US 7,282,580 B2
(45) Date of Patent: Oct. 16, 2007

(54) PROTEIN MOLECULE USEFUL FOR INHIBITION OF ANTHRAX TOXIN

(75) Inventors: Yogendra Singh, Delhi (IN); Hemant Khanna, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/780,250

(22) Filed: Feb. 17, 2004

(65) Prior Publication Data

US 2004/0235136 A1    Nov. 25, 2004

Related U.S. Application Data

(63) Continuation-in-part of application No. 09/821,348, filed on Mar. 29, 2001, now abandoned.

(51) Int. Cl.
*C07H 21/04* (2006.01)

(52) U.S. Cl. ............ 536/23.7; 514/44; 435/71.1; 435/69.3; 435/69.1; 530/350

(58) Field of Classification Search ............ None
See application file for complete search history.

(56) References Cited

U.S. PATENT DOCUMENTS

| | | | |
|---|---|---|---|
| 4,264,588 A | | 4/1981 | Orcutt |
| 5,591,631 A | | 1/1997 | Leppla et al. |
| 6,329,156 B1 | | 12/2001 | Cirino et al. |
| 6,592,872 B1 | * | 7/2003 | Klimpel et al. ........ 424/197.11 |
| 2002/0048590 A1 | * | 4/2002 | Klimpel et al. ........ 424/246.1 |
| 2003/0198651 A1 | * | 10/2003 | Klimpel et al. ........ 424/246.1 |

OTHER PUBLICATIONS

*Sirard, J et al, (1997, reference of record.).*
Sellman, B.R., et al.; Point Mutations in Anthrax Protective Antigen That Block Translation; Mar. 16, 2001; The Journal of Biological Chemistry; vol. 276(11); pp. 8371-8376.
Sirard, J., et al.; A Recombinant Bacillus Anthracis Strain Producing the Clostridium Perfringens ib Component Induces Protection Against Iota Toxins; Jun. 1997; Infection and Immunity; vol. 65(6); pp. 2029-2033.
Billington, S.J., et al.; Infection and Immunity; vol. 66(9); pp. 4531-4536; Sep. 1998.
Marvaud, J., et al.; Infection and Immunity; vol. 69(4); pp. 2435-2441; Apr. 2001.
Stiles, B.G. et al.; Infection and Immunity; vol. 68(6); pp. 3475-3484; Jun. 2000.
Petosa, C., et al.; Nature; vol. 385; pp. 833-838; Feb. 27, 1997.
Price, L.B., et al.; Journal of Bacteriology; vol. 181(8); pp. 2358-2362; Apr. 1999.
Swiss Prot Accession No. Q46221; Release date Nov. 1, 1996; Iota Toxin Component Ib.
Swiss-Prot Accession No. P13423; Release date Jan. 13, 1990; Anthrax Protective Antigen.
Perelli, S., et al.; Characterization of Clostridium Perfringens Iota-Toxin Genes and Expression in *Escherichia coli*;Published erratum appears in Infect. Immun. 1995; Dec. 63(12):4967.

* cited by examiner

*Primary Examiner*—L. J. Smith
*Assistant Examiner*—Ginny Allen Portner
(74) *Attorney, Agent, or Firm*—Mathews, Shepherd, McKay & Bruneau, P.A.

(57) ABSTRACT

The present invention relates to a novel molecule useful for anthrax toxin inhibition in vivo and also provides a method for in vivo inhibition of anthrax toxin action using the new molecule.

4 Claims, 4 Drawing Sheets

|        | 1 | 2 | 3 |
|--------|---|---|---|
| 182    | — |   |   |
| 118    | — |   |   |
| 85.2   | — | — | — |
| 62.5   | — |   |   |
| 58.5   | — |   |   |
| 47     | — |   |   |

PROTEIN MOLECULE USEFUL FOR INHIBITION OF ANTHRAX TOXIN

This application is a continuation-in-part of U.S. application Ser. No. 09/821,348, which was filed on Mar. 29, 2001 now abandoned.

FIELD OF THE INVENTION

The present invention relates to a novel molecule useful for the inhibition of anthrax toxin. The invention also provides a method for inhibition of anthrax toxin action using the new molecule. The main utility of the invention is to develop a candidate molecule for anthrax toxin inhibition and for providing a method for inactivation of toxic activity of a toxin of the nature of anthrax toxin. This molecule has potential for use as A therapeutic agent in neutralizing anthrax toxin action in individuals infected with Bacillus anthracis.

BACKGROUND OF THE INVENTION

Anthrax is a bacterial disease caused by Bacillus anthracis. The disease primarily affects herbivores but humans can also get infected while dealing with such animals. B. anthracis is a potential agent of bio-terrorism. Main symptoms comprise dizziness, fever, edema followed by death. The toxic action of anthrax has been attributed to anthrax toxin produced by the bacterium. The toxin can be resolved into three distinct protein components protective antigen (PA), lethal factor (LF) and edema factor (EF). The combination of EF and PA (edema toxin) produces skin edema, while LF and PA (Lethal toxin) are lethal to animals. The three proteins are individually non-toxic. EF is a calcium and calmodulin dependent adenylate cyclase that acts by increasing the intracellular cAMP levels in eukaryotic cells and LF is a $Zn^{2+}$ dependent metalloprotease that leads to increase in IL-1 and TNF-α production by susceptible cells and cleaves several MAP Kinase Kinases (MKK 1, 2 and 3) (Leppla, 1999).

According to the current model of anthrax toxin action, PA binds to anthrax toxin receptor present on cell surface and gets proteolytically activated by cell surface proteases to PA63. This allows oligomerization and binding of LF/EF. The toxin complex is internalized by receptor mediated endocytosis and is exposed to acidic pH inside the endosome. This change in pH triggers both membrane insertion by PA63 and translocation of LF/EF into the cytosol (Leppla, 1999).

Membrane insertion and channel formation are brought about by a large 2β2–2β3 loop (amino-acid residues 302–325) in the domain II of PA (Petosa et al., 1997). The loop shows a conserved pattern of alternating hydrophilic and hydrophobic amino-acid residues similar to that observed in Clostridium perfringens iota-b toxin. PA has also been shown to possess high degree of homology with the iota-b toxin (Perelle et al., 1993).

Translocation of LF/EF to the cytosol is believed to occur through a channel formed by insertion of heptameric PA63 into the membrane. The formation of ion-conductive channels by PA63 has been demonstrated in both artificial lipid membranes and in CHO-K1 cells. Acidic pH triggers stable oligomerization, membrane insertion by PA63 and translocation of LF into the cytosol of mammalian cells.

A recombinant vaccine candidate, PA-D, in which furin cleavage site of PA was deleted has been reported by Singh et al., 1989. This recombinant protein (PA-D) was completely non-toxic to macrophage like cell lines as well as when administered in Fischer 344 rats in combination with LF whereas wild-type PA plus LF killed the rats within 60 min. PA-D blocked the action of anthrax toxin albeit at higher concentrations than the wild-type protein due to which this molecule does not seem to be an effective inhibitor of anthrax toxin action. Hence need exists to develop a more potent candidate molecule such as dominant negative inhibitor for anthrax toxin inhibition. No report on dominant negative inhibition of anthrax toxin action exists.

Sirard et al (1997) discloses a recombinant protein that comprises "amino acid residues of amphiphatic loop of iot-toxin" wherein the recombinant protein is produced through fusion of Bacillus anthraces pag gene promoter to the iota-toxin Ib gene. While the claimed molecule, PA-I is mutant version of PA, where only 23 amino acid have been used from iota-b-toxin and the resulting molecule behaves like a dominant negative inhibitor of anthrax toxin. The present invention is not a full length iota-b-toxin. Thus the recombinant protein is totally different.

Sellman et al (2001) discloses a dominant mutant inhibitor of PA, wherein the molecule comprises an amino acid residues present in 2B2–2B3 loop of iota-b-toxin, wherein PA evidenced a mutation with a change from phenylalanine to alanine. Both molecules i.e. PA-I and the molecule developed by Sellman are derived from PA only but still they differ significantly in their sequences. PA-I has 23 amino acids from iota-b toxin while the molecule developed by Sellman et al has only one mutation in PA protein. The region where it differs in PA is also different. It is very clear that these both molecules are distinct. The main feature of the invention is replacement of bolded part of PA sequence with blue part of the iota b toxin sequence to get the PA-I.

Here we describe for the first time, a novel mutant PA protein which obviates the drawback listed above. It acts as a dominant negative inhibitor of anthrax toxin action. The protein is completely non-toxic both in vitro and in vivo and completely inhibits the lethal effect of the native toxin at equimolar concentrations. This molecule is a better substitute for in vivo inhibition of anthrax toxin in comparison to PA-D since it can inhibit the action of anthrax toxin when present at equimolar or substantially lower concentrations than wild-type protein.

No such molecule has been reported for inactivation of anthrax toxin action. The approach taken herein for inactivation of anthrax toxin action is a novel one.

OBJECTS OF THE INVENTION

The main object of the invention is to provide a novel molecule for anthrax toxin inhibition.

Another object is to provide a method for inactivation of toxic activity of a toxin of the nature similar to that of anthrax toxin.

Yet another object of the invention is to provide a therapeutic agent for use in neutralizing anthrax toxin action in individuals infected with Bacillus anthracis.

Anthrax is a bacterial disease caused by a gram-positive bacteria Bacillus anthracis which affects cattle and humans. Major virulence factor of B. anthracis is a tripartite protein exotoxin called anthrax toxin which consists of three proteins: protective antigen (PA), lethal factor (LF) and edema factor (EF).

The present invention provides a candidate molecule, recombinant protective antigen, useful for anthrax toxin inhibition comprising a protein designated as PA-I, wherein the 2β2–2β3 loop containing the residues of the amphipathic loop of the homologous iota-b toxin.

Also is provided DNA sequence of the mutated gene encoding the recombinant protein The invention also provides a method for construction of the recombinant protein which comprises PCR based mutagenesis of PA gene resulting into dominant negative mutant of PA, purification of mutant PA protein from *B. anthracis*, cytotoxicity assay, in vitro inhibition of pore-forming ability of wild-type PA by PA-I for demonstrating defective channel formation followed by competitive inhibition assay for checking the equivalent activity of the native toxin on mammalian cells and assaying for inhibition of the wild-type toxic activity of anthrax toxin in vivo.

BRIEF DESCRIPTION OF THE FIGURES

Figure 1:
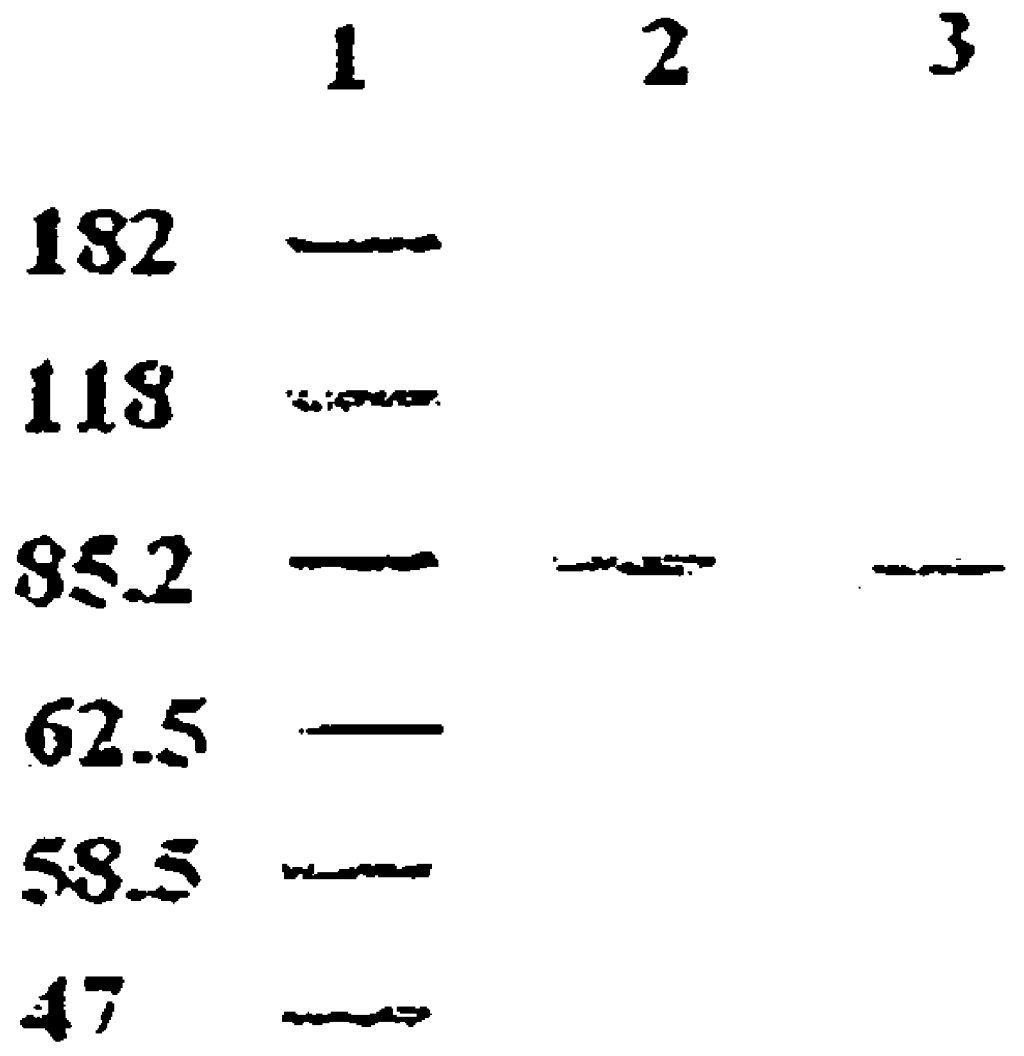

FIG. 1: PA and PA-I were purified from the cell supernatants of *B. anthracis* and analyzed on 10% SDS-PAGE. Lane 1: Molecular Weight Marker (kDa); Lane 2: Native PA; Lane 3: PA-I

Figure 3:
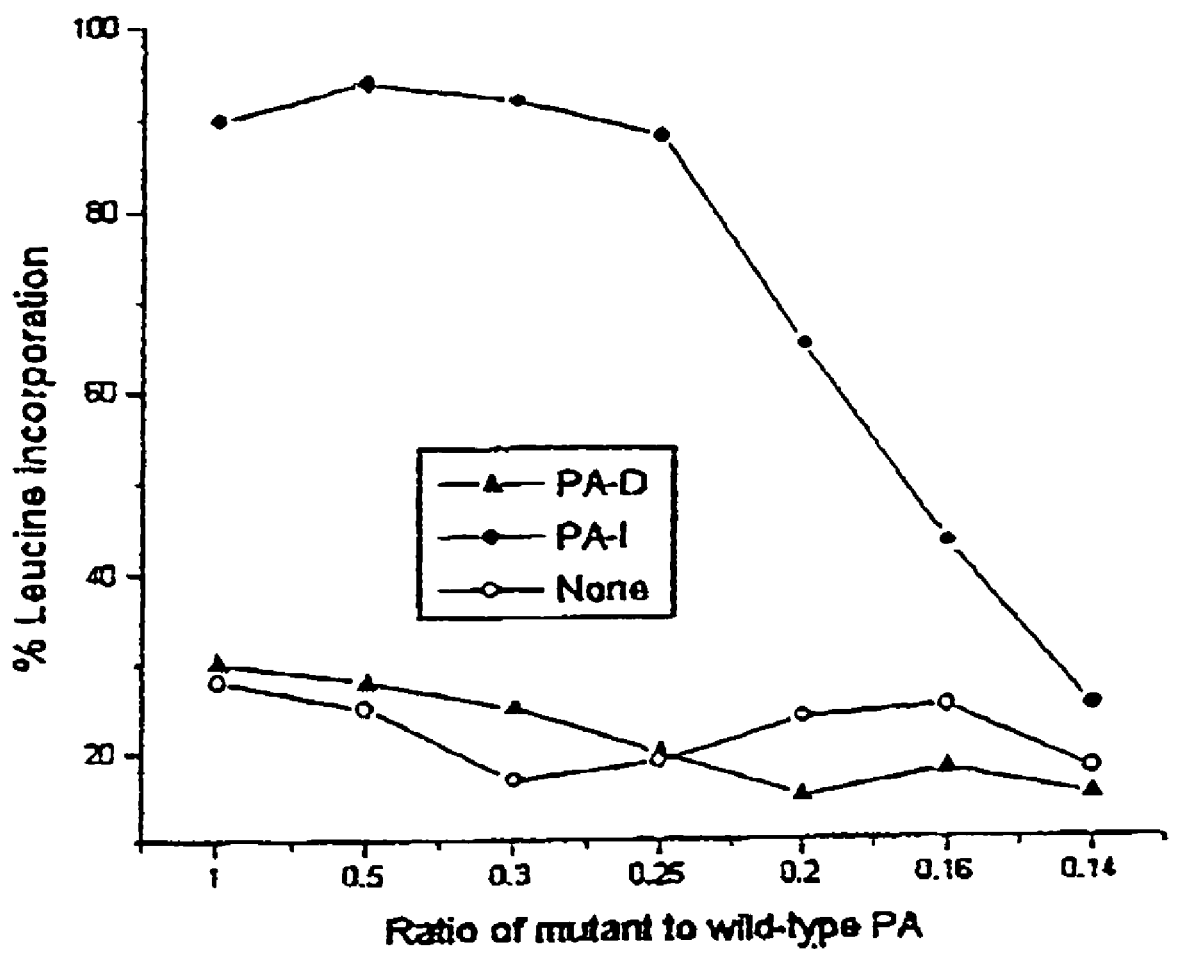

FIG. 3: CHO-K1 cells were incubated with PA-I or PA-D mixed with varying concentrations of wild type PA at 37° C. for 3 h in combination with $LF^{1-254}.TR.PE^{398-613}$. At the end of 3 h, cells were incubated with medium containing $^3$H-leucine (1 µCi/ml) for 1 h at 37° C. At the end of the experiment, amount of $^3$H-leucine incorporation was measured. Results are expressed as percentage of $^3$H-leucine incorporated by viable cells in the absence of added proteins.

DETAILED DESCRIPTION OF THE INVENTION

Figure 2:
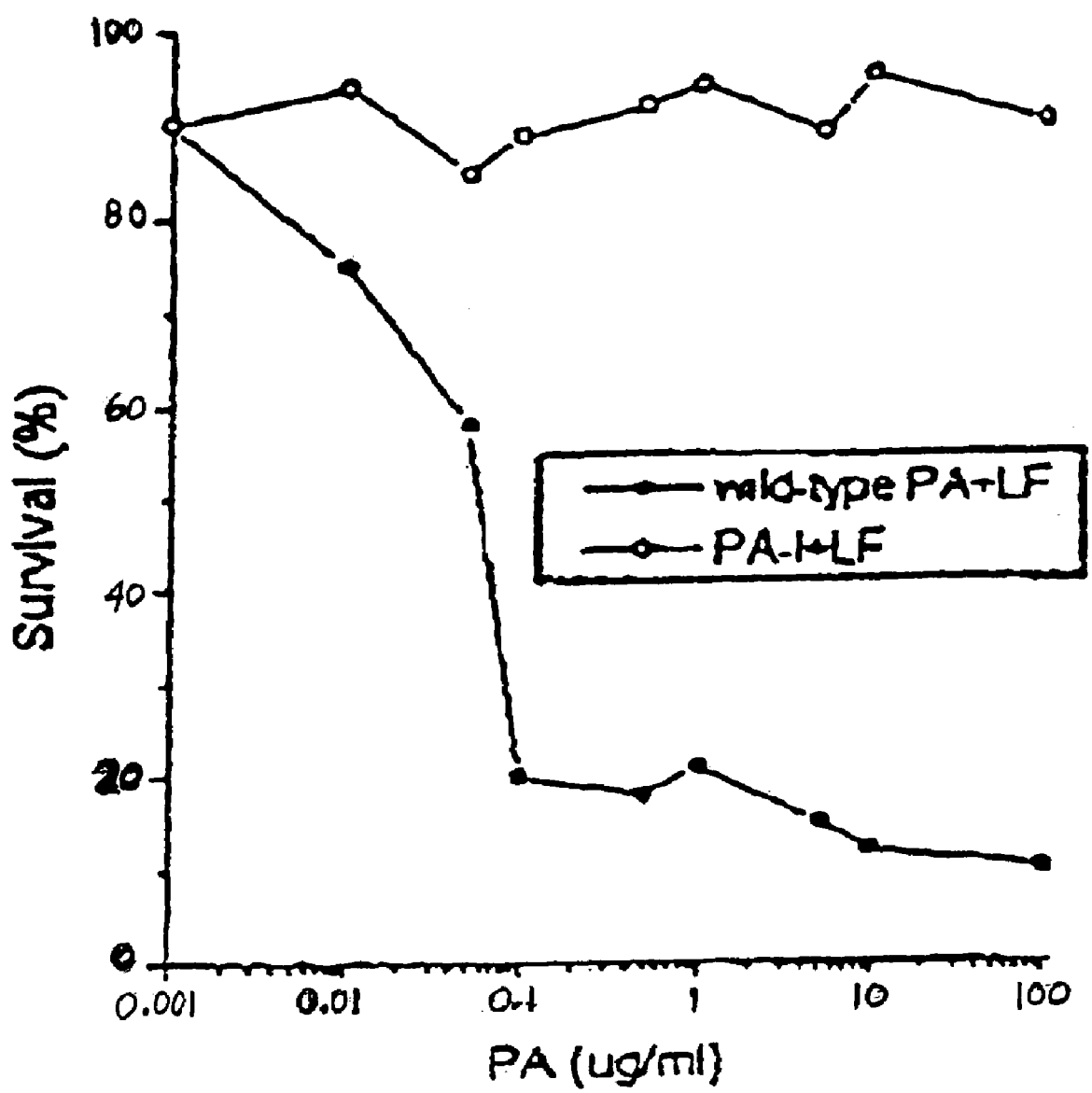
FIG. 2: J774A.1 cells were cultured in 96 well plates in DMEM containing 10% fetal bovine serum and incubated with LF (1 µg/ml) in combination with varying concentrations of PA and PA-I for 3 h at 37° C. At the end of the experiment, toxicity was determined by MTT assay.

The present invention provides a novel molecule, said molecule being a recombinant protective antigen and useful for anthrax toxin inhibition.

In an embodiment of the present invention the recombinant protein designated as PA-I of SEQ ID NO:1, useful for inhibiting anthrax toxin.

In another embodiment of the present invention recombinant protein is non toxic to host cells.

In still another embodiment of the present invention the recombinant protein inhibits native protein Protective Antigen (PA) mediated cellular intoxication.

In an embodiment of the present invention the recombinant protein inhibits the channel forming ability of PA protein.

Yet in another embodiment of the present invention the recombinant protein when applied with PA in the ratio of about 1:1, completely inhibits the anthrax lethal toxin.

Yet in another embodiment of the present invention the recombinant protein PA-I has oligopeptide of SEQ ID NO:2 instead of oligopeptide of SEQ ID NO:3 of native PA.

Yet in another embodiment of the present invention the gene encoding the recombinant protein (PA-I), having sequence SEQ ID NO:4.

Still in another embodiment of the present invention the oligonucleotide primers of SEQ ID NO:5 and SEQ ID NO:6.

In another embodiment of the present invention the site of mutation itself is of 69 bp and some flanking region on both sides of this has been taken into consideration to prepare the Primer of SEQ ID NO:5.

In one more embodiment of the present invention the SEQ ID NO:5 is reverse primer while SEQ ID NO:6 is forward primer.

Further in another embodiment of the present invention, wherein process for constructing a recombinant protein PA-I comprising steps:
i) amplifying a region of PA gene encoding 2β2–2 β3 loop using the primers of SEQ ID NO:5 and SEQ ID NO:6;
ii) mutating the amplified PA gene by replacing SEQ ID NO:3 of native PA with SEQ ID NO:2,
iii) cloning the amplified mutated PA gene of step (ii) into a vector, and
iv) expressing the clone in a host to obtain the recombinant protein PA-I.

In another embodiment of the present invention, wherein the host used is selected from a group comprising *E. coli*, *Bacillus anthracis* etc.

Still in another embodiment of the present invention, wherein the vector for cloning the mutant gene is selected from a group of expression vector comprising plasmid pYS5 and pMS 1.

Yet in another embodiment of the present invention, wherein the concentration of PA-I used for testing anthrax toxin inhibition is in the range of 0.01 µg/ml to 0.1 µg/ml.

In another embodiment of the present invention a composition useful in inhibiting anthrax toxin, said composition comprising a recombinant protein PA-I of SEQ ID NO:1 and pharmacologically acceptable additive(s).

Still in another embodiment of the present invention, a method of treating anthrax infection in a subject in need thereof, said method comprising step of administering an effective amount of PA-I in pharmacologically acceptable additive(s).

Yet in another embodiment of the present invention a method of treatment, wherein the fluid is glucose or PBS.

Further in another embodiment of the present invention, wherein the PA-I is administered intravenously.

Yet in another embodiment of the present invention, wherein the subject is mammals, preferably human.

Yet in another embodiment of the present invention, wherein the recombinant protein PA-I completely inhibits the toxicity of anthrax lethal toxin.

Still in another embodiment of the present invention, wherein recombinant protein PA-I results in 100% survival of rats even after 72 hours of injecting the toxin.

In one more embodiment of the present invention, wherein recombinant protein PA-I inhibits the pore formation by native PA in cells. The changes in the amino-acid sequence in this loop have rendered it non-toxic and imparted a dominant negative phenotype consequently inhibiting the anthrax toxin action. The mutagenesis of the PA gene in this region has caused inhibition of pore-forming ability of wild-type PA by PA-I by defective channel formation.

In yet another embodiment of the invention, in vivo system used to test the in vivo anthrax toxin inhibitory effect can be Fischer 344 rats, guinea pigs, mice and the like.

The vector for cloning the mutant gene may be any expression vector such as plasmid pYS5, pMS1, and the like.

In still another embodiment of the invention, mammalian cell lines used can be CHO-K1, J774A. 1, RAW 264.7 and the like.

Further aspects, features and advantages of the present invention will be apparent from the following description of the presently preferred embodiments of the invention given for the purpose of disclosures. The invention is further established with the help of following examples. The examples should not be construed to limit the scope the invention.

EXAMPLE 1

Reagents

Bio-chemicals and reagents were purchased from Sigma Chemical Co., St. Louis, USA. Bacterial culture media was purchased from Difco Laboratories, Becton Dickinson, Delhi, India. The enzymes and chemicals for DNA manipulations were obtained from New England BioLabs, USA. $^3$H-Leucine were obtained from Amersham Pharmacia Biotech, Piscataway, N.J., USA.

The Chinese Hamster Ovary cell line (CHO-K1) and J774A.1 macrophage cell line were maintained in Dulbecco's Modified Eagle's Medium (DMEM) supplemented with 10% calf serum and 50 µg/ml gentamicin sulfate (Life Technologies, Inc., USA) at 37° C. in a $CO_2$ incubator.

EXAMPLE 2

Construction of the mutant PA Gene

Figure 4:
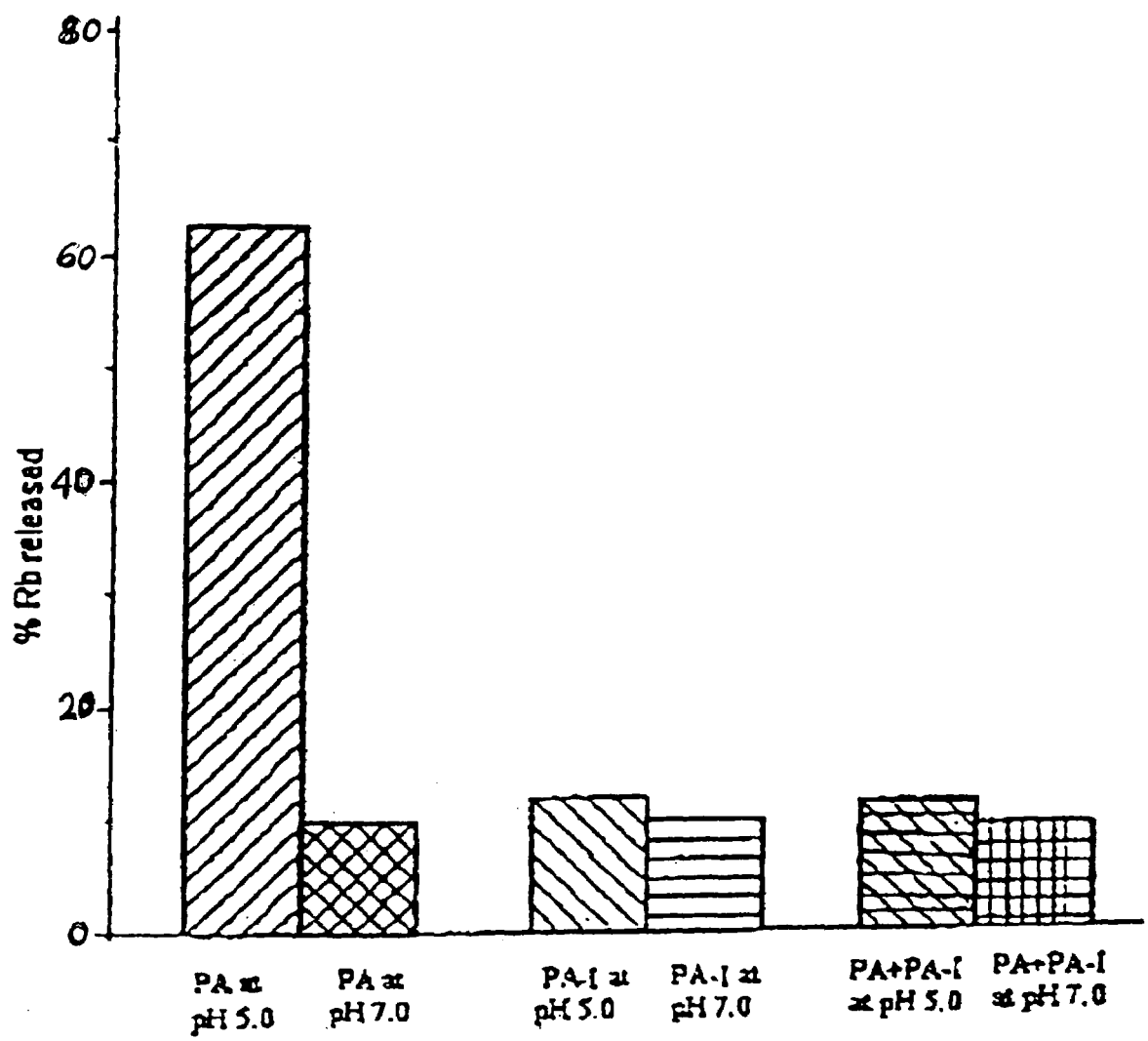
FIG. 4: CHO-K1 cells, preloaded with $^{86}Rb^+$, were incubated with trypsin cleaved PA and PA-I mixed in equimolar ratios at neutral pH for 2 h at 4° C. After washing twice with cold phosphate buffered saline, the cells were subjected to acidic pH shock. The leakage of $^{86}Rb^+$ into the medium was then determined. Results are expressed as percentage of $^{86}Rb^+$ associated with cells in the absence of added proteins.

Mutation in the PA gene was constructed in the plasmid pYS5 (Singh et al., 1989). A non-mutagenic oligonucleotide primer corresponding to nucleotides 2176–2198 and spanning the unique HindIII site was used for PCR with a mutagenic primer corresponding to nucleotides 2759–2868 encompassing the unique PstI site and containing the desired mutations at nucleotides 2782–2850 (nucleotide numbering is according to Welkos et al., 1988). PCR was performed in a 100 ul tube at the following conditions (30 cycle):

94° C.: 1 min.
94° C.: 30 sec
55° C.: 1 min
72° C.: 1 min
72° C.: 10 min
4° C.: 1 h The constituents of the reaction were:

10×PCR buffer: 1×
Template DNA: 0.5 μg
Forward primer: 0.5 μM
Reverse Primer: 0.5 μM
dNTPs: 20 μM
Taq DNA polymerase: 2.5 U/μl The amplified PCR product was digested with PstI and HindIII as describer below:

10× Buffer: 1×
Template: 10 μg
PstI: 10 U/μl
HindIII: 10U/μl and purified on a 1% low melting point agarose gel. The DNA sample was dissolved in 6× sample buffer (final concentration 1×), loaded on low melting point agarose gel and run at 50V. The plasmid pYS5 was digested with the same enzymes, purified on agarose gel and ligated to the mutant fragment. The DNA sequence of the mutant PA gene was verified by DNA sequencing of at least 200 base pairs spanning the mutated region.

EXAMPLE 3

Expression and Purification of Recombinant Protein PA-I

The plasmid carrying the desired sequence was transformed into *E. coli* dam dcm strain SCS110. Unmethylated plasmid DNA was purified and used to transform *B. anthracis* BH441. *B. anthracis* was transformed by adding 2 μg of DNA into electrocompetent cells and exposing them to a voltage of 1.5 kV and resistance of 200 Ω. The transformed culture was grown overnight and the cell supernatant was concentrated using concentrator and the protein analyzed using SDS-PAGE.

EXAMPLE 4

Molecular Weight Determination

The molecular weight of PA-I was determined by SDS-PAGE (Laemmli, 1970). The protein sample (2 μg) was dissolved in 5×SDS dye (final concentration 1×) and run on the 10% gel. The molecular weight of PA-I was found to be equal to that of native PA (83 kDa) as determined by SDS-PAGE using appropriate molecular weight standards (FIG. 1).

EXAMPLE 5

Cytotoxicity Assay

To study the cytotoxicity, varying concentrations of PA and PA-I were added to J774A. 1 cells together with LF (1.0 μg/ml) and incubated for 3 h at 37° C. At the end of the experiment, cell viability was determined using MTT assay (Singh et al., 1994). The result showed that the mutant PA protein PA-I is completely non-toxic to J774A.1 cells (FIG. 2).

EXAMPLE 6

Inhibition of the Activity of Native PA by PA-I

Inhibition of activity of native PA by PA-I was investigated by mixing of the mutant PA protein and native type PA at varying ratios resulted in alterations in the cyto-toxic activity of the toxin containing the native protein (PA plus LF). When the mutant and native PA were present at equimolar concentrations, complete inhibition in protein synthesis of CHO-K1 cells was observed. A significant inhibition could be detected when the ratio of PA-I to PA was 1:4. These data suggest that the PA-I inhibits native PA mediated cellular intoxication (FIG. 3).

EXAMPLE 7

Inhibition of Pore Forming Ability of Native PA by PA I

Recombinant protein (PA-I) and the native protein (PA) were mixed together (2 μg/ml each) at the neutral pH and incubated with CHO-K1 cells preloaded with $^{86}Rb^+$ at 4° C. After 2 h, the cells were washed to remove unbound proteins and incubated with isotonic buffer of pH 5.0 or 7.0 for 30 min. at 37° C. Whereas native PA released 62% of the radiolabel from cells, equimolar mixture containing PA and PA-I showed insignificant release of $^{86}Rb^+$. The results suggest that there is complete inhibition of channel forming ability of PA by PA-I (FIG. 4). The capacity of PA-I to dramatically alter the channel forming ability of native PA provides evidence that these two species can interact to form dysfunctional hetero-oligomeric structures.

EXAMPLE 8

In Vivo Inhibition of Anthrax Toxin Activity

Animal experiments were performed to test the efficacy of PA-I to act as a dominant negative inhibitor of lethal toxin action in vivo (that is in equimolar concentration with respect to native PA. Native lethal toxin (40 μg PA+8 μg LF) resulted in the death of male Fischer 344 rats in approximately 60 min. (Table 1), whereas a 1:1 mix containing native PA and PA-I (40 μg PA+40 μg PA-I+8 μg LF) protected rats and no symptoms were evident even after 48 h. Equimolar ratio of native PA and PA-D resulted in the death of rats within 70 minutes.

TABLE 1

Inhibitory action of PA-I on Fischer 344 rats.

| PA (μg) | LF (μg) | PA-I (μg) | PA-D (μg) | TTD[a] |
|---|---|---|---|---|
| 40 | — | — | — | Survived |
| — | 8 | — | — | Survived |
| 40 | 8 | — | — | 60 min. |
| 40 | 8 | — | 40 | 70 min. |
| 40 | 8 | 40 | — | Survived |

[a]TTD is the time to death of Fischer 344 rats after administration of proteins.

What is claimed is:

1. An isolated polynucleotide encoding a recombinant protein which is useful for inhibiting anthrax toxin, the recombinant protein comprising SEQ ID NO 1.

2. An isolated DNA vector comprising the polynucleotide of claim 1.

3. An isolated transformed host cell comprising the polynucleotide of claim 1.

4. An isolated protein comprising SEQ ID NO 1, produced by the expression of the polynucleotide of claim 1.

* * * * *

```
                        SEQUENCE LISTING

<160> NUMBER OF SEQ ID NOS: 6

<210> SEQ ID NO 1
<211> LENGTH: 735
<212> TYPE: PRT
<213> ORGANISM: Artificial Sequence
<220> FEATURE:
<223> OTHER INFORMATION: Derived from B. anthracis.

<400> SEQUENCE: 1

Glu Val Lys Gln Glu Asn Arg Leu Leu Asn Glu Ser Glu Ser Ser Ser
 1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
        35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125

Gly Leu Asp Phe Lys Leu Tyr Trp Thr Asp Ser Gln Asn Lys Lys Glu
    130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
                165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
        195                 200                 205

Asn Ile His Glu Lys Lys Gly Leu Thr Lys Tyr Lys Ser Ser Pro Glu
```

-continued

```
            210                 215                 220
Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
                245                 250                 255

Ala Ala Tyr Pro Ile Val His Val Asp Met Glu Asn Ile Ile Leu Ser
                260                 265                 270

Lys Asn Glu Asp Gln Ser Thr Gln Asn Thr Asp Ser Gln Thr Arg Thr
            275                 280                 285

Ile Ser Lys Asn Thr Ser Thr Ser Arg Asp Ala Asn Thr Val Gly Val
            290                 295                 300

Ser Ile Ser Ala Gly Tyr Gln Asn Gly Phe Thr Gly Asn Ile Thr Thr
305                 310                 315                 320

Ser Ala Gly Phe Ser Asn Ser Asn Ser Ser Thr Val Ala Ile Asp His
                325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
            355                 360                 365

Thr Gly Thr Ala Pro Ile Tyr Asn Val Leu Pro Thr Thr Ser Leu Val
370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
                405                 410                 415

Ala Pro Ile Ala Leu Asn Ala Gln Asp Asp Phe Ser Ser Thr Pro Ile
                420                 425                 430

Thr Met Asn Tyr Asn Gln Phe Leu Glu Leu Glu Lys Thr Lys Gln Leu
            435                 440                 445

Arg Leu Asp Thr Asp Gln Val Tyr Gly Asn Ile Ala Thr Tyr Asn Phe
            450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
                485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
            515                 520                 525

Ile Ala Phe Gly Phe Asn Glu Pro Asn Gly Asn Leu Gln Tyr Gln Gly
530                 535                 540

Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
                565                 570                 575

Val Leu Asp Lys Ile Lys Leu Asn Ala Lys Met Asn Ile Leu Ile Arg
                580                 585                 590

Asp Lys Arg Phe His Tyr Asp Arg Asn Asn Ile Ala Val Gly Ala Asp
            595                 600                 605

Glu Ser Val Val Lys Glu Ala His Arg Glu Val Ile Asn Ser Ser Thr
            610                 615                 620

Glu Gly Leu Leu Leu Asn Ile Asp Lys Asp Ile Arg Lys Ile Leu Ser
625                 630                 635                 640
```

```
Gly Tyr Ile Val Glu Ile Glu Asp Thr Glu Gly Leu Lys Glu Val Ile
                645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
        675                 680                 685

Ile Ser Asn Pro Asn Tyr Lys Val Asn Val Tyr Ala Val Thr Lys Glu
    690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
                725                 730                 735
```

<210> SEQ ID NO 2
<211> LENGTH: 23
<212> TYPE: PRT
<213> ORGANISM: Artificial Sequence
<220> FEATURE:
<223> OTHER INFORMATION: Derived from B. anthracis.

<400> SEQUENCE: 2

```
Asp Ala Asn Thr Val Gly Val Ser Ile Ser Ala Gly Tyr Gln Asn Gly
1               5                   10                  15

Phe Thr Gly Asn Ile Thr Thr
            20
```

<210> SEQ ID NO 3
<211> LENGTH: 23
<212> TYPE: PRT
<213> ORGANISM: Bacillus anthracis

<400> SEQUENCE: 3

```
Thr His Thr Ser Glu Val His Gly Asn Ala Glu Val His Ala Ser Phe
1               5                   10                  15

Phe Asp Ile Gly Gly Ser Val
            20
```

<210> SEQ ID NO 4
<211> LENGTH: 69
<212> TYPE: DNA
<213> ORGANISM: Artificial Sequence
<220> FEATURE:
<223> OTHER INFORMATION: Synthetic.

<400> SEQUENCE: 4
gatgctaata ctgtaggagt ttcaatttca gcagggtatc agaacggctt tactggtaat    60
atcactaca                                                           69

<210> SEQ ID NO 5
<211> LENGTH: 110
<212> TYPE: DNA
<213> ORGANISM: Artificial Sequence
<220> FEATURE:
<223> OTHER INFORMATION: Synthetic.

<400> SEQUENCE: 5
attactaaat cctgcagatg tagtgatatt accagtaaag ccgttctgat accctgctga    60
aattgaaact cctacagtat tagcatccct acttgtagaa gtattttac              110

<210> SEQ ID NO 6

-continued

```
<211> LENGTH: 23
<212> TYPE: DNA
<213> ORGANISM: Artificial Sequence
<220> FEATURE:
<223> OTHER INFORMATION: Synthetic.

<400> SEQUENCE: 6
gtgattaata aagcttctaa ttc                                              23
```